US012775115B2

(12) United States Patent
Sowards et al.

(10) Patent No.: US 12,775,115 B2
(45) Date of Patent: Oct. 27, 2026

(54) MAGNETIC SIGNATURE IDENTIFICATION SYSTEM

(71) Applicant: Bard Access Systems, Inc., Salt Lake City, UT (US)

(72) Inventors: Steffan Sowards, Salt Lake City, UT (US); William Robert Mclaughlin, Bountiful, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 129 days.

(21) Appl. No.: 17/949,679

(22) Filed: Sep. 21, 2022

(65) Prior Publication Data

US 2023/0102059 A1 Mar. 30, 2023

Related U.S. Application Data

(60) Provisional application No. 63/250,022, filed on Sep. 29, 2021.

(51) Int. Cl.

*G01V 3/08* (2006.01)
*A61B 5/055* (2006.01)
*G01V 3/38* (2006.01)

(52) U.S. Cl.

CPC .............. *G01V 3/081* (2013.01); *A61B 5/055* (2013.01); *G01V 3/38* (2013.01)

(58) Field of Classification Search

CPC ........... A61B 5/055; G01V 3/081; G01V 3/38
See application file for complete search history.

(56) References Cited

U.S. PATENT DOCUMENTS 4,940,966 A * 7/1990 Pettigrew .............. H01F 10/132 340/572.6
10,188,310 B2 * 1/2019 Derichs .................. G01R 33/02
(Continued)

FOREIGN PATENT DOCUMENTS

EP 2997901 A1 3/2016
WO 2013034175 A1 3/2013
(Continued)

OTHER PUBLICATIONS

PCT/US2022/044234 filed Sep. 21, 2022 International Search Report and Written Opinion dated Dec. 16, 2022.
(Continued)

*Primary Examiner* — Gregory H Curran
(74) *Attorney, Agent, or Firm* — Rutan & Tucker LLP

(57) ABSTRACT

Disclosed herein is a magnetic signature identification system. The system can include a magnetic signature identification device having one or more magnetometers configured to detect magnetic characteristics defined by magnetic elements including dipoles coupled with a target medical device. Logic, when executed by one or more processors, determines a magnetic signature of the target medical device based upon a magnetic field defined by the magnetic characteristics. The system may include multiple medical devices having distinct magnetic signatures stored in memory and the logic may determine an identity of the target medical device by a comparison of the magnetic signature of the target medical device with the distinct magnetic signatures. The magnetic characteristics may be defined by any combination of all or any subset of the number, length, spacing, or orientation of the dipoles. The magnetic signature identification system may be coupled with a device tracking system and/or other medical system.

27 Claims, 6 Drawing Sheets

(56) References Cited

U.S. PATENT DOCUMENTS

| | | | |
|---|---|---|---|
| 11,281,869 | B2 * | 3/2022 | Vartiovaara ............ G06K 7/087 |
| 2002/0171547 | A1 | 11/2002 | Johnston et al. |
| 2003/0094487 | A1 | 5/2003 | Blankenship et al. |
| 2007/0114786 | A1 | 5/2007 | Antonenco et al. |
| 2008/0041248 | A1 | 2/2008 | Kuwabara et al. |
| 2009/0012418 | A1 | 1/2009 | Gerlach |
| 2011/0148414 | A1 | 6/2011 | Teughels et al. |
| 2013/0029112 | A1 | 1/2013 | Bargir et al. |
| 2014/0253270 | A1 | 9/2014 | Nicholls et al. |
| 2014/0290512 | A1 | 10/2014 | Raksha |
| 2014/0299668 | A1 | 10/2014 | Fullerton et al. |
| 2015/0178522 | A1 | 6/2015 | Cato et al. |
| 2016/0008091 | A1 | 1/2016 | Saotome et al. |
| 2016/0262844 | A1 * | 9/2016 | Cohen .................... A61B 5/062 |
| 2017/0238996 | A1 | 8/2017 | Frame et al. |
| 2017/0347914 | A1 * | 12/2017 | Isaacson .............. A61B 8/0841 |
| 2018/0117419 | A1 | 5/2018 | Jackson |
| 2018/0221610 | A1 | 8/2018 | Larson et al. |
| 2018/0310955 | A1 | 11/2018 | Lindekugel et al. |
| 2020/0250385 | A1 | 8/2020 | Narayanan et al. |
| 2020/0298493 | A1 | 9/2020 | Wilds et al. |
| 2020/0360662 | A1 | 11/2020 | Ma et al. |
| 2020/0405406 | A1 | 12/2020 | Harris et al. |
| 2021/0113113 | A1 * | 4/2021 | Weprin .................. G01V 13/00 |
| 2021/0174378 | A1 | 6/2021 | Rahimizad et al. |
| 2023/0096231 | A1 | 3/2023 | McLaughlin et al. |
| 2023/0101371 | A1 | 3/2023 | Sowards et al. |
| 2023/0285096 | A1 | 9/2023 | Lambrecht et al. |
| 2023/0334502 | A1 | 10/2023 | Top et al. |
| 2025/0182946 | A1 | 6/2025 | McLaughlin et al. |
| 2026/0038724 | A1 | 2/2026 | Sowards et al. |

FOREIGN PATENT DOCUMENTS

| | | | |
|---|---|---|---|
| WO | 2023055628 | A1 | 4/2023 |
| WO | 2023055821 | A1 | 4/2023 |
| WO | 2023055958 | A1 | 4/2023 |

OTHER PUBLICATIONS

PCT/US2022/045069 filed Sep. 28, 2022 International Search Report and Written Opinion dated Mar. 14, 2023.

PCT/US2022/045264 filed Sep. 29, 2022 International Search Report and Written Opinion dated Jan. 27, 2023.

PCT/US2022/044234 filed Sep. 21, 2022 International Preliminary Report on Patentability dated Apr. 2, 2024.

U.S. Appl. No. 17/955,120, filed Sep. 28, 2022 Notice of Allowance dated Sep. 25, 2024.

U.S. Appl. No. 17/956,651, filed Sep. 29, 2022 Non-Final Office Action dated Nov. 14, 2024.

U.S. Appl. No. 17/956,651, filed Sep. 29, 2022 Final Office Action dated Apr. 17, 2025.

U.S. Appl. No. 17/956,651, filed Sep. 29, 2022 Notice of Allowance dated Jul. 14, 2025.

U.S. Appl. No. 19/044,191, filed Feb. 3, 2025 Notice of Allowance dated Feb. 25, 2026.

* cited by examiner

MAGNETIC SIGNATURE IDENTIFICATION SYSTEM

PRIORITY

This application claims the benefit of priority to U.S. Provisional Application No. 63/250,022, filed Sep. 29, 2021, which is incorporated by reference in its entirety into this application.

BACKGROUND

Medical errors continue to be a significant source of injury to a patient undergoing a medical treatment. As such, reducing medical errors continues to be a priority in the medical industry. The use of incorrect devices, drugs, etc. contribute to these medical errors. Many medical injuries are the result of human error. Utilizing technology to identify the devices, drugs, etc. for a given procedure has shown to significantly decrease the rate of medical errors. Magnetic elements of a medical device have enabled the medical device to be tracked in three-dimensional space. However, the tracking of medical devices via magnetic elements only partially utilizes the magnetic technology. It would be beneficial to the use magnetic technology to identify medical devices and thereby reduce the probability of using an incorrect device. Disclosed herein systems, devices, and methods that utilize magnet technology to addresses the foregoing.

SUMMARY

Disclosed herein is a medical system that, according to some embodiments, includes a target medical device having a number of magnetic elements that define a magnetic signature, and a magnetic signature identification device. The magnetic signature identification device includes one or more magnetometers configured to detect a number of magnetic fields defined by the magnetic elements and a console coupled with the one or more magnetometers, where the console includes one or more processors, an energy source, and a non-transitory computer-readable medium having logic stored thereon that, when executed by the processors perform operations, where the operations include (i) receiving electrical signals from the one or more magnetometers, the electrical signals based on the magnetic fields; and (ii) determining the magnetic signature from the electrical signals.

In some embodiments of the system, the magnetic elements include a number of dipoles defining a number of magnetic characteristics detectable by the one or more magnetometers. In some embodiments of the system, the magnetic elements are imprinted on the target medical device.

In some embodiments of the system, the magnetic signature is defined by two or more magnetic characteristics selected from the group consisting of: the number of dipoles on the target medical device, a position of one or more of dipoles on the target medical device, a length of one or more of dipoles extending along the target medical device, and an orientation of one or more of the dipoles with respect to an orientation of the target medical device.

In some embodiments of the system, the magnetic signature identification device is employed by another medical device or system.

In some embodiments of the system, the other medical device or system is selected from a group consisting of an ultrasound probe, an ultrasound system, and a patient sensor.

In some embodiments of the system, the determining the magnetic signature includes at least one of: determining the number two or more dipoles; determining the orientation of two or more dipoles; determining the length of at least one dipole; or determining the position of at least one dipole with respect to at least one other dipole.

In some embodiments of the system, the determining the magnetic signature includes at least two of: determining the number two or more dipoles; determining the orientation of two or more dipoles; determining the length of at least one dipole; or determining the position of at least one dipole with respect to at least one other dipole.

In some embodiments of the system, the operations further include (i) comparing the magnetic signature with a stored magnetic signature in the non-transitory computer-readable medium, where the stored magnetic signature is linked to a defined medical device identity; and (ii) as a result of the comparison, determining that an identity of target medical device is the same as the defined medical device identity when the magnetic signature is the same as (or similar to) the stored magnetic signature. In some embodiments of the system, the operations further include communicating the identity of target medical device to the other medical device or system.

In some embodiments, the system further includes a plurality of medical devices, where each one of the plurality of medical devices includes a magnetic signature distinct from the magnetic signatures of the other ones of the plurality of medical devices, and where the target medical device is chosen from the plurality of medical devices.

In some embodiments of the system, the magnetic signature identification device is coupled with a medical device tracking system configured to track the location of the target medical device in three-dimensional space via the magnetic signature.

In some embodiments of the system, the medical device tracking system is configured to track two or more target medical devices simultaneously, where each of the two or more target medical devices has a magnetic signature that is distinct from the other target medical devices.

Also disclosed herein is a method performed by a medical system of identifying a target medical device. According to some embodiments, the method includes (i) detecting a magnetic field caused by magnetic elements of a target medical device; (ii) determining from the magnetic field, a magnetic signature of the target medical device; (iii) comparing the magnetic signature determined from the magnetic field with a magnetic signature stored in memory of the system, where the magnetic signature stored in memory is linked to a defined medical device identity; and (iv) as a result of the comparison, determining that an identity of the target medical device is the same as the defined medical device identity.

In some embodiments of the method, the magnetic elements of the target medical device include a number of dipoles located on the target medical device. In some embodiments of the method, determining the magnetic signature includes determining the number of dipoles. In some embodiments of the method, determining the magnetic signature includes determining a position of a first dipole on the target medical device with respect to a position of a second dipole on the target medical device.

In some embodiments of the method, determining the magnetic signature includes (i) determining a length of a third dipole on the target medical device, and (ii) determining a length of a fourth dipole on the target medical device, where the length of the fourth dipole is different from the length of the third dipole.

In some embodiments of the method, determining the magnetic signature includes (i) determining an orientation of a fifth dipole on the target medical device; and determining an orientation of a sixth dipole on the target medical device, where the orientation of the sixth dipole is different from the orientation of the fifth dipole.

In some embodiments of the method, the system includes a plurality of medical devices, where each one of the plurality of medical devices includes a magnetic signature distinct from the magnetic signatures of the other ones of the plurality of medical devices, and where the target medical device is chosen from the plurality of medical devices.

In some embodiments of the method, the system includes a medical device tracking system configured to track the location of the target medical device in three-dimensional space via the magnetic signature, and the method further includes tracking the location of the target medical device in three-dimensional space via the magnetic signature.

In some embodiments of the method, the medical device tracking system is configured to track two or more target medical devices simultaneously, and the method further includes (i) tracking a location of a first target medical device via a magnetic signature of the first target medical device; and (ii) tracking a location of a second target medical device via a magnetic signature of the second target medical device, where the magnetic signature of the second target medical device is distinct from the magnetic signature of the first target medical device.

Also disclosed herein is a medical device, that according to some embodiments, includes a plurality of magnetic elements coupled to a body of the medical device, where the magnetic elements define a magnetic signature of the medical device. The medical device is one of a plurality of medical devices of a medical system, where each medical device includes a magnetic signature that is distinct from the magnetic signatures of the other medical devices of the system. In some embodiments of the device, the magnetic elements are imprinted on the medical device.

In some embodiments of the device, the magnetic elements include a number of dipoles defining a number of magnetic characteristics of the magnetic signature. In some embodiments of the device, the magnetic characteristics include the number of dipoles. In some embodiments of the device, the magnetic characteristics include a relative position on the medical device of one dipole with respect to at least one other dipole. In some embodiments of the device, the magnetic characteristics include a length of the dipoles. In some embodiments of the device, the magnetic characteristics include an orientation of the dipoles.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
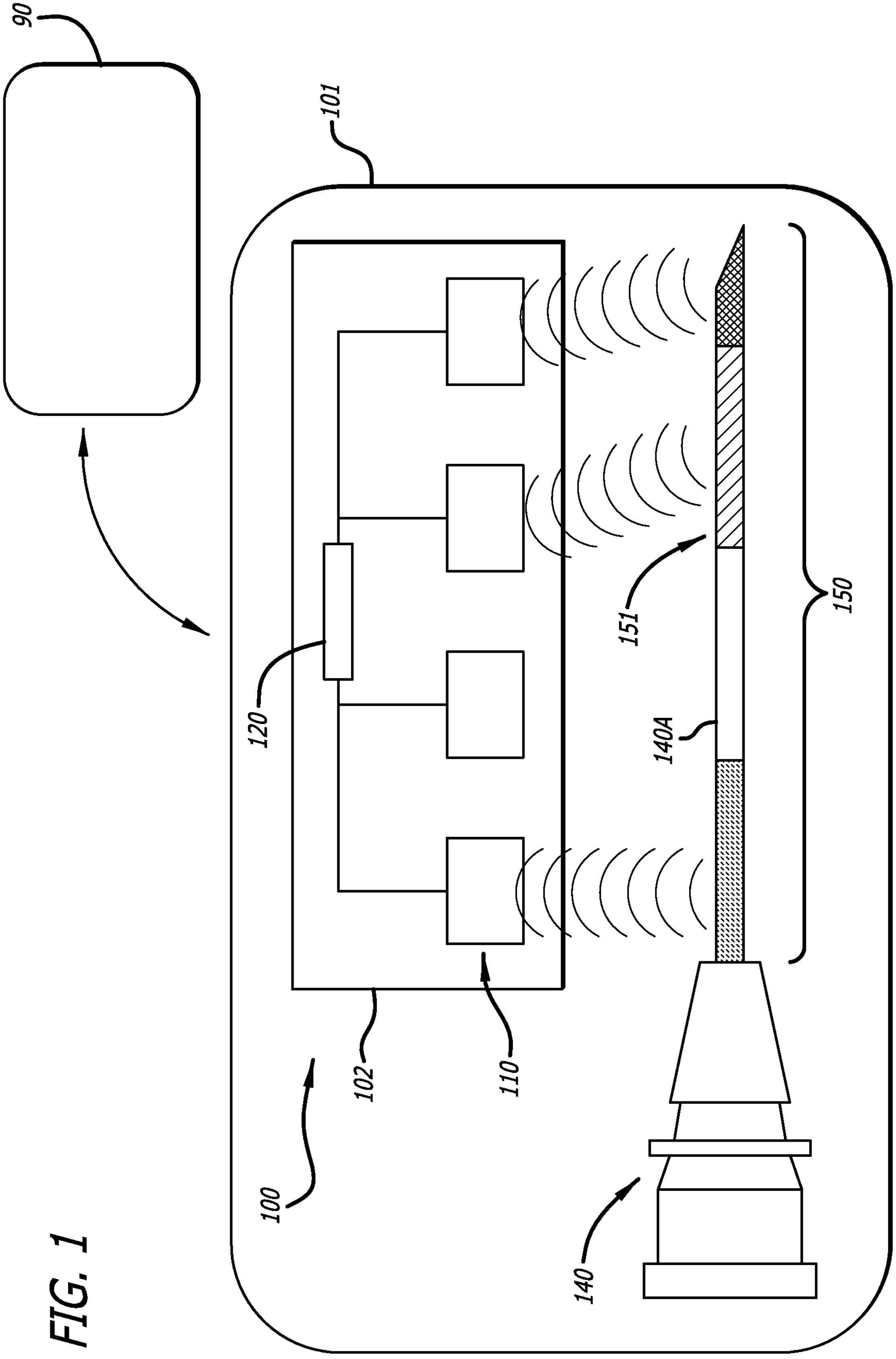
FIG. 1 illustrates a plan view of a magnetic signature identification system, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The phrases "connected to," "coupled with," and "in communication with" refer to any form of interaction between two or more entities, including but not limited to mechanical, electrical, magnetic, electromagnetic, fluid, and thermal interaction. Two components may be coupled with each other even though they are not in direct contact with each other. For example, two components may be coupled to each other through an intermediate component.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Unless defined otherwise, all technical and scientific terms used herein have the same meaning as commonly understood by those of ordinary skill in the art.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

FIG. 1 illustrates a plan view of a magnetic signature identification system (system) 100, in accordance with some embodiments. The system 100 is generally configured to identify a medical device via magnetic technology. In some embodiments, the system 100 includes a magnetic signature identification device 102 having one or more magnetometers 110 configured to identify a target medical device 140 by detecting a magnetic signature 150 of the target medical device 140. The target medical device 140 includes magnetic elements 151 (e.g., ferrous elements) that define a magnetic signature 150. The magnetic elements 151 may be imprinted on or otherwise coupled with the target medical device 140 or more specifically a body 140A of the target medical device 140. In some embodiments, a portion of or the entire target medical device 140 may be passed through a magnetic field to imprint the magnetic signature 150 upon the ferrous elements of the target medical device 140.

In some embodiments, the magnetic signature identification device 102 may be integrated into, or otherwise coupled with, a medical device tracking system 101, where the medical device tracking system 101 is configured to track the target medical device 140 having magnetic signature 150 in three-dimensional space. In some embodiments, the magnetic signature 150 may be distinctly different for multiple target medical devices 140. As such, the medical device tracking system 101 may be configured to track multiple target medical devices 140, simultaneously. In some embodiments, the medical device tracking system 101 maybe coupled to or integrated into another medical device or system 90, such as a ultrasound imaging system, for example.

The magnetic signature 150 may include an identity of the target medical device 140. In some embodiments, the magnetic signature 150 may define a distinct type of the target device 140, such as a needle, a stylet, a guidewire, an obturator, a probe, a tunneller, a stent, a port, a balloon device, a sheath, or any other type of medical device without limit. In some embodiments, the magnetic signature 150 may define distinct models of a target device type, such as via a specific model number, for example. In some embodiments, the magnetic signature 150 may define a manufacturing history of the target medical device 140, such as a specific manufacturing date, a lot number, or other device history record information, for example. In some embodiments, the magnetic signature 150 may define a unique serial number or other unique identifying entity. As such, in some embodiments, a target medical device 140 may include a magnetic signature 150 that is unique with respect to all other magnetic signatures 150.

Variations of detectable characteristics may distinguish one magnetic signature 150 from another magnetic signature 150, thus distinguishing the identity of one target medical device 140 from another target medical device 140. For example, the target medical device 140 may be a guidewire having a magnetic signature 150 thereon and an associated medical device may be an ultrasound probe having the magnetic signature identification device 102 coupled thereto. The magnetic signature identification device 102 may determine the identity of the target medical device 140 as a guidewire via the magnetic signature 150 when the guidewire is brought into proximity of the magnetic signature identification device 102. The magnetic signature identification device 102 may then communicate the identity of the target medical device 140 to the medical device or system 90 or the medical device tracking system 101.

The magnetic signature 150 generally includes a number (e.g., 1, 2, 3, 4 or more) of detectable magnetic characteristics. The magnetic signature 150 is defined by one or more magnetic dipoles, where each dipole includes a North pole and South pole defining an orientation of the dipole. In some embodiments, the one or more dipoles may include passive magnets coupled with the target device or imprinted magnetic elements of the target medical device 140. The one or more dipoles define a number of magnetic characteristics detectable by magnetic field sensors. For example, the characteristics may include the number of dipoles and/or the position of the dipoles on the target device. Further, each dipole may define additional characteristics, such as a length of the dipole, an orientation of the dipole, and/or magnetic strength of the dipole, for example. The magnetic signature 150 may be defined by a single characteristic or any combination of two or more characteristics.

The magnetic signature 150 may be configured to also provide an identity of the target medical device 140 to the medical device tracking system 101. As such, the medical device tracking system 101 may identify the target medical device 140 as well as track the location of the target medical device 140.

The magnetic signature identification device 102 may include a console 120 coupled with the one or more magnetometers 110. In some embodiments, the one or more magnetometers 110 may be arranged in array. The one or more magnetometers 110 may be configured to detect and communicate the various detectable characteristics of the magnetic signature 150 to the console 120, wherein the logic of console 120 may determine the identity of the target medical device 140, as will be described in more detail herein. In some embodiments, the magnetic signature identification device 102, including one or more magnetometers 110 and the console 120, may be coupled to, integrated into, or otherwise employed with the medical device or system 90, where the medical device or system 90 includes a probe, an ultrasound probe, an ultrasound system module, a patient sensor, or any other medical device or system. In other embodiments, the magnetic signature identification device 102 may include separate module, such as a standalone module, a remote module, or a patch cable module, for example.

Figure 2:
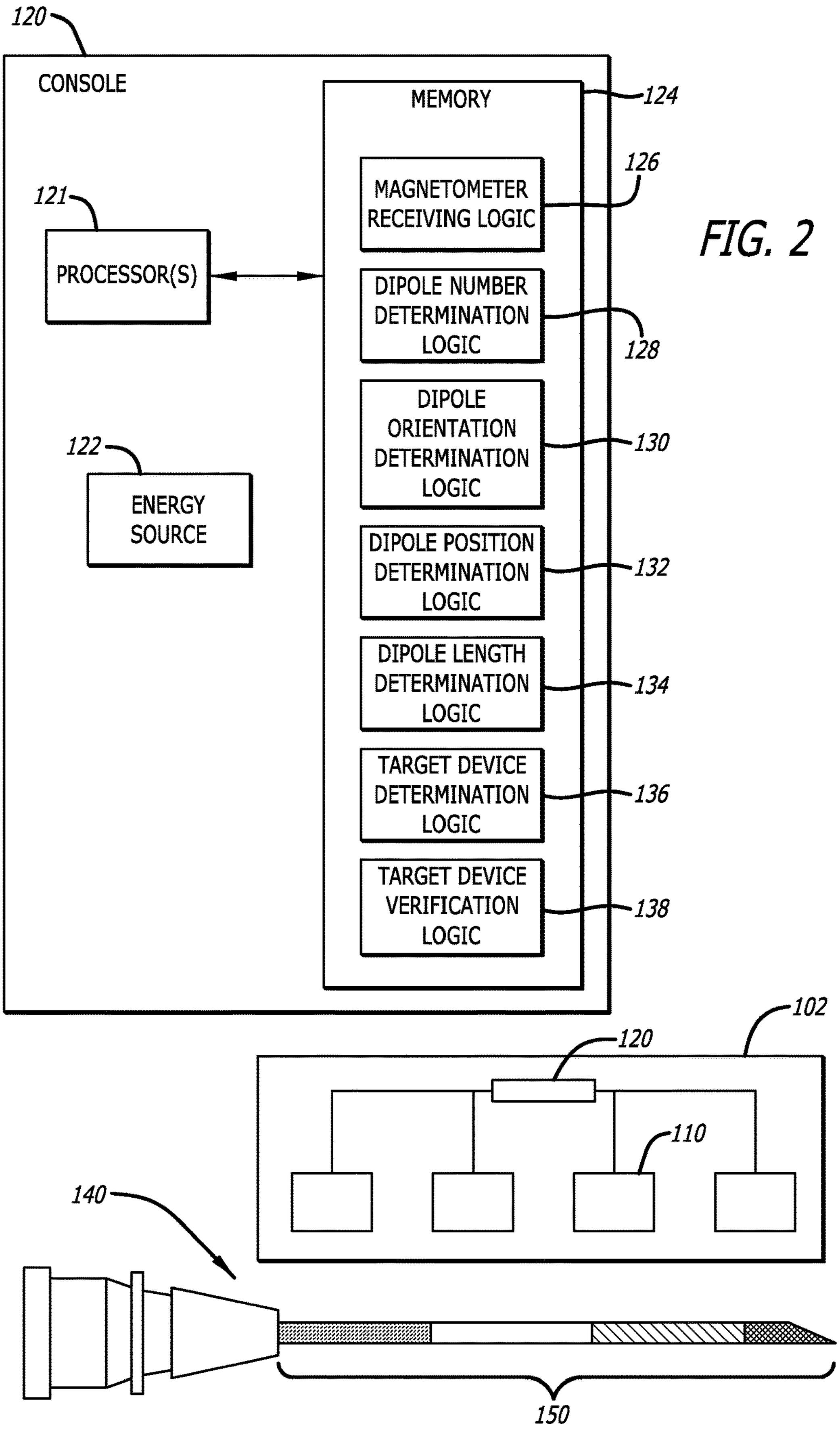
FIG. 2 illustrates a block diagram of some components of the magnetic signature identification system of FIG. 1 including a console, in accordance with some embodiments.

FIG. 2 illustrates a block diagram of some components of the magnetic signature identification system 100, including the console 120, in accordance with some embodiments. In some embodiments, the console 120 includes one or more processors 121, an energy source 122, non-transitory computer-readable medium ("memory") 124 and logic (e.g., a plurality of logic modules). In some embodiments, the energy source 122 may be configured to provide power to the one or more magnetometers 110. In some embodiments, the plurality of logic modules may include a magnetometer receiving logic 126, a dipole number determination logic 128, a dipole orientation determination logic 130, a dipole position determination logic 132, a dipole length determination logic 134, a target device determination logic 136, and a target device verification logic 138. In some embodiments, the magnetometer receiving logic 126 may be configured to receive magnetometer values corresponding to one or more of (i) the number of dipoles detected on the target medical device 140, (ii) the orientation of the detected dipoles, (iii) the position on the target medical device 140 of the dipoles, or (iv) the length of the dipoles on the target medical device 140. In some embodiments, each magnetometer of the one or more magnetometers 110 may detect and communicate separate magnetometer values to the console 120. In some embodiments, the magnetometer receiving logic 126 may be configured to receive the magnetometer values from each magnetometer 110 separately.

In some embodiments, the dipole number determination logic 128 may be configured to determine the number of dipoles detected by each of the one or more magnetometers 110 using the magnetometer values received from each of the magnetometers 110. In some embodiments, the dipole orientation determination logic 130 may be configured to determine the orientation of each of the detected dipoles using the magnetometer values received from each of the magnetometers 110. In some embodiments, the orientation of the each of the dipoles includes detection of the direction of the North/South poles. In some embodiments, the dipole position determination logic 132 may be configured to determine the position of each of the one or more dipoles on the target medical device 140 using the magnetometer values detected from each of the magnetometers 110. For example, the target medical device 140 may include a first dipole located at a distal tip, a second dipole located at a proximal end, and a third dipole located at a midpoint between the proximal end and the distal tip. The dipole position determination logic 132 may be configured to determine the location of the three dipoles. The location of the dipoles may be a location of the any subset of dipoles with respect to any other subset of dipoles or with respect to the body 140A of the target medical device 140.

In some embodiments, the dipole length determination logic 134 may be configured to determine the length of each of the one or more dipoles using the magnetometer values from each of the magnetometers 110. In some embodiments, the target device determination logic 136 may be configured to use two or more of: the number of detected dipoles, the orientation of each of the detected dipoles, the location of each of the dipoles, or the length of each of the detected dipoles to determine the identity of the target medical device 140. In some embodiments, the target device determination logic 136 may compare the number of detected dipoles, the orientation of each of the detected dipoles, the location of each of the dipoles, and the length of each of the detected dipoles to a database of known target medical devices having known magnetic signatures.

In some embodiments, each of the magnetometer receiving logic 126, the dipole number determination logic 128, the dipole orientation determination logic 130, the dipole position determination logic 132, and the dipole length determination logic 134 may be configured to generate output values used as input values for the target device identification logic 136 to determine the identity of the target medical device 140. For example, the dipole number determination logic 128 may generate a dipole number value, the dipole orientation determination logic may generate a dipole orientation value for each detected dipole, the dipole position determination logic may generate a dipole position value for each detected dipole, and the dipole length determination logic may generate a dipole length value for each detected dipole. The values may be stored and referenced as {dipole number value, first dipole orientation value, first dipole position value, first dipole length value, second dipole orientation value, second dipole position value, second dipole length value, etc.}.

In some embodiments, the target device verification logic 138 may be configured to verify the identity of the target medical device 140. In some embodiments, the target device verification logic 138 may prompt a user to verify that the identity of the target medical device 140 as detected by the system 100 is the same identity of target medical device 140 being used. In some embodiments, the target device verification logic 138 may be configured to compare the detected magnetic signature with known magnetic signatures stored in memory. As a result of the comparison, the target device verification logic 138 may determine that the detected magnetic signature is the same as or otherwise consistent at least one known magnetic signature stored in memory.

Figure 3A:
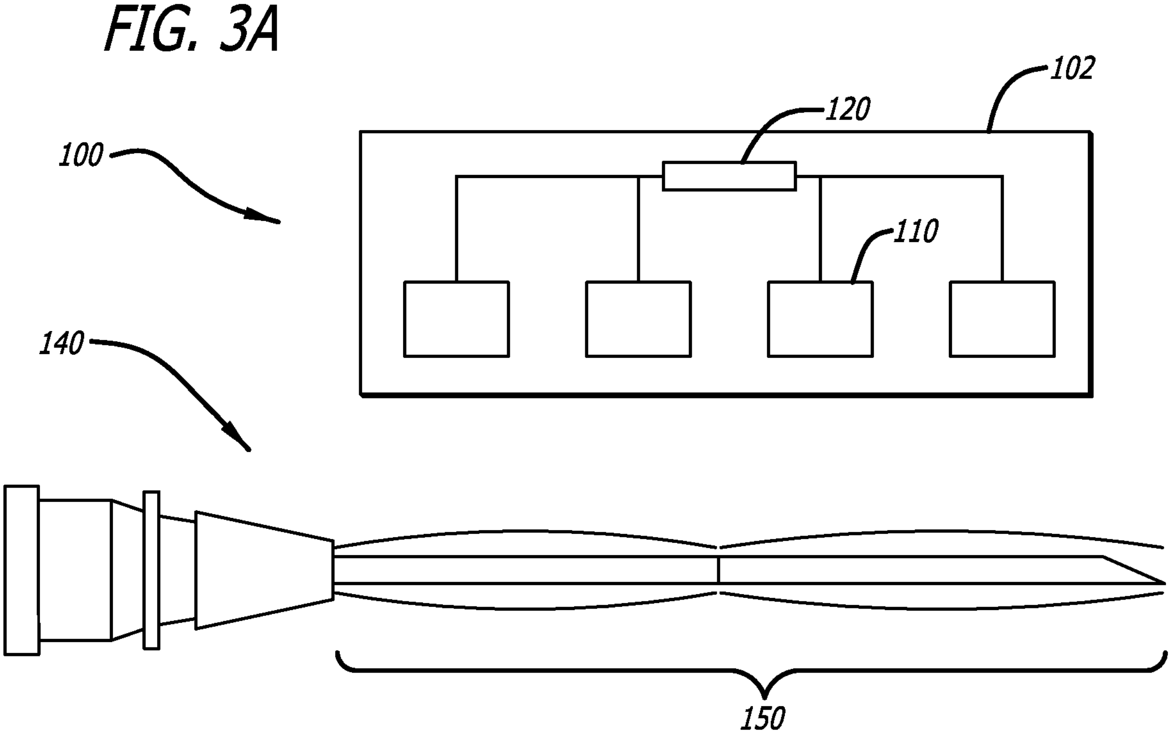
FIGS. 3A-3D are various plan views of the system of FIG. 1 illustrating exemplary methods of identifying a target medical device based upon a magnetic signature, in accordance with some embodiments.

FIGS. 3A-3D illustrate various examples of an exemplary method of identifying the target medical device 140 based upon the magnetic signature 150 using the magnetic signature identification system 100, in accordance with some embodiments. According to one example, as illustrated in FIG. 3A, the target medical device 140 may include the magnetic signature 150 and may be located proximate the magnetic signature identification device 102. In some embodiments, the magnetic signature identification device 102 may be coupled to a medical device. The one or more magnetometers 110 in communication with the console 120 may detect two dipoles of equal length. The logic of console 120 may determine via the number of detected dipoles and the length of the dipoles that the target medical device 140 is a stylet.

Figure 3B:
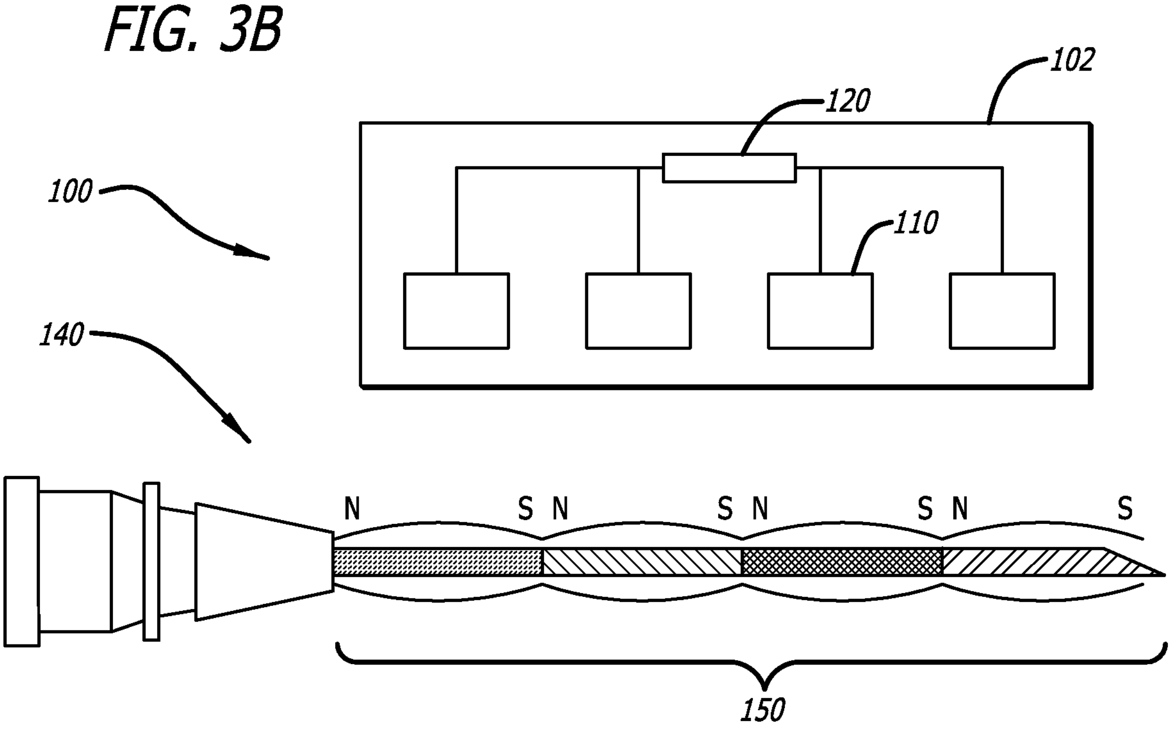

According to another example, as illustrated in FIG. 3B, the target medical device 140 includes the magnetic signature 150 and may be located proximate the magnetic signature identification device 102. In some embodiments, the magnetic signature identification device 102 may be coupled to or integrated into a medical device. The one or more magnetometers 110 in communication with the console 120 may detect four distinct dipoles, wherein three of the four dipoles have the same length and all four dipoles have the same orientation (e.g., North to South). The logic of the console 120 may determine via the number, the orientation, and the length of the dipoles that the target medical device 140 is a needle.

Figure 3C:
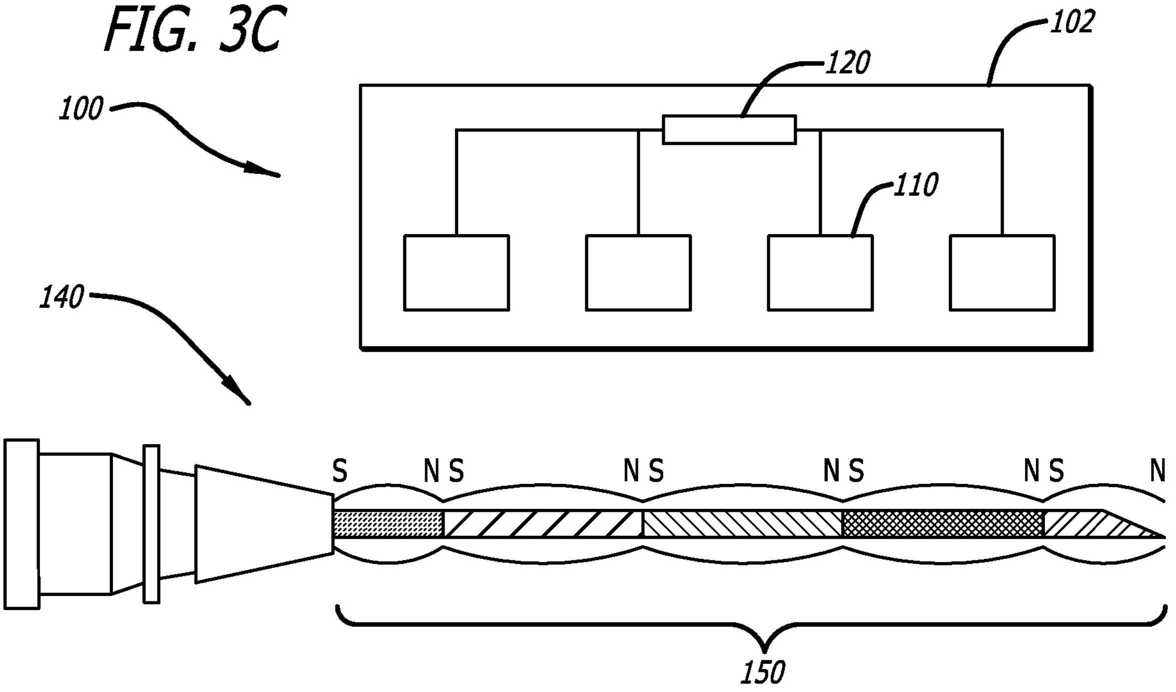

According to another example, as illustrated in FIG. 3C, the target medical device 140 includes the magnetic signature 150 and may be located proximate the magnetic signature identification device 102. In some embodiments, the magnetic signature identification device 102 may be coupled to or integrated into a medical device. The one or more magnetometers 110 in communication with the console 120 may detect five distinct dipoles, wherein three of the five dipoles have the same length and all four dipoles have the same orientation (e.g., South to North). The logic of console 120 may determine via the number, the orientation, and the length of the dipoles that the target medical device 140 is a needle.

Figure 3D:
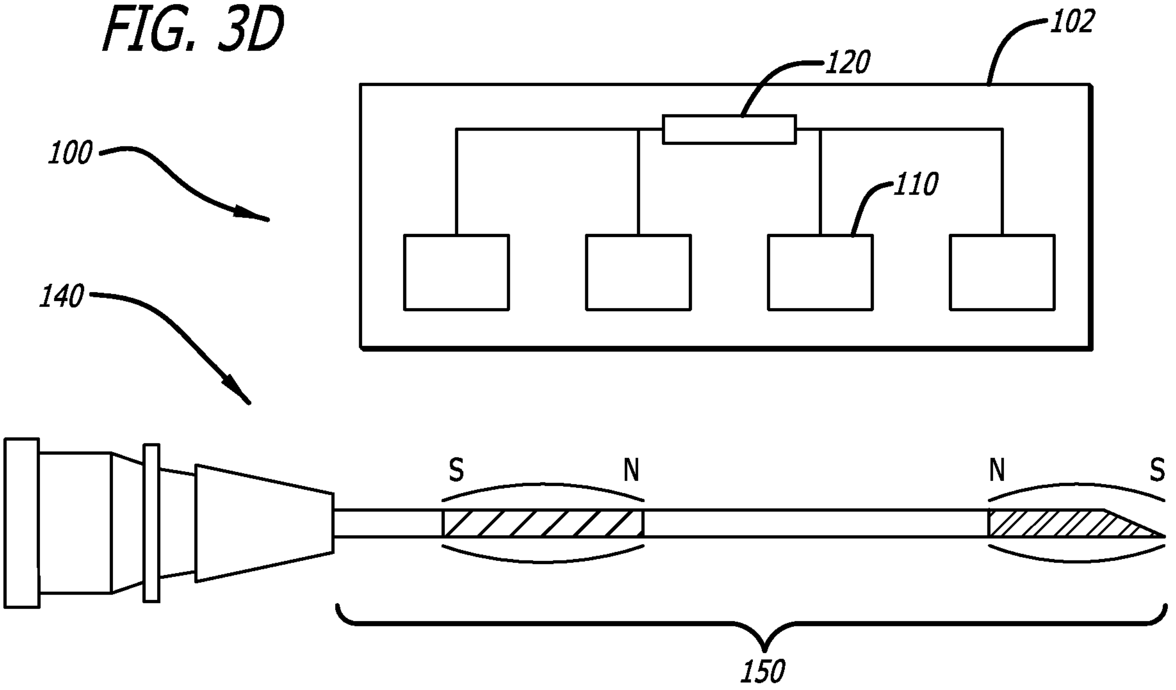

According to another example, as illustrated in FIG. 3D, the target medical device 140 includes the magnetic signature 150 and may be located proximate the magnetic signature identification device 102. In some embodiments, the magnetic signature identification device 102 may be coupled to or integrated into a medical device. The one or more magnetometers 110 in communication with the console 120 may be configured to detect two distinct dipoles, one dipole at a distal tip and one dipole more proximal on the target medical device 140. The magnetometers may detect the two dipoles have opposing orientations. The logic of the console 120 may determine via the number, the orientation, and the position of the dipoles that the identity of the target medical device 140 is a needle.

In some embodiments, target devices 140 of similar identities may have similar characteristics that make up their magnetic signature 150. For example, stylets may all have dipoles at the same position, but the orientation of the dipoles, the length of the dipoles, and the number of dipoles may be different for each type of stylet. Similar target devices 140 having similar characteristics that make up their magnetic signature 150 may allow the system 100 to quickly detect the identity of the target medical device 140.

Figure 4:
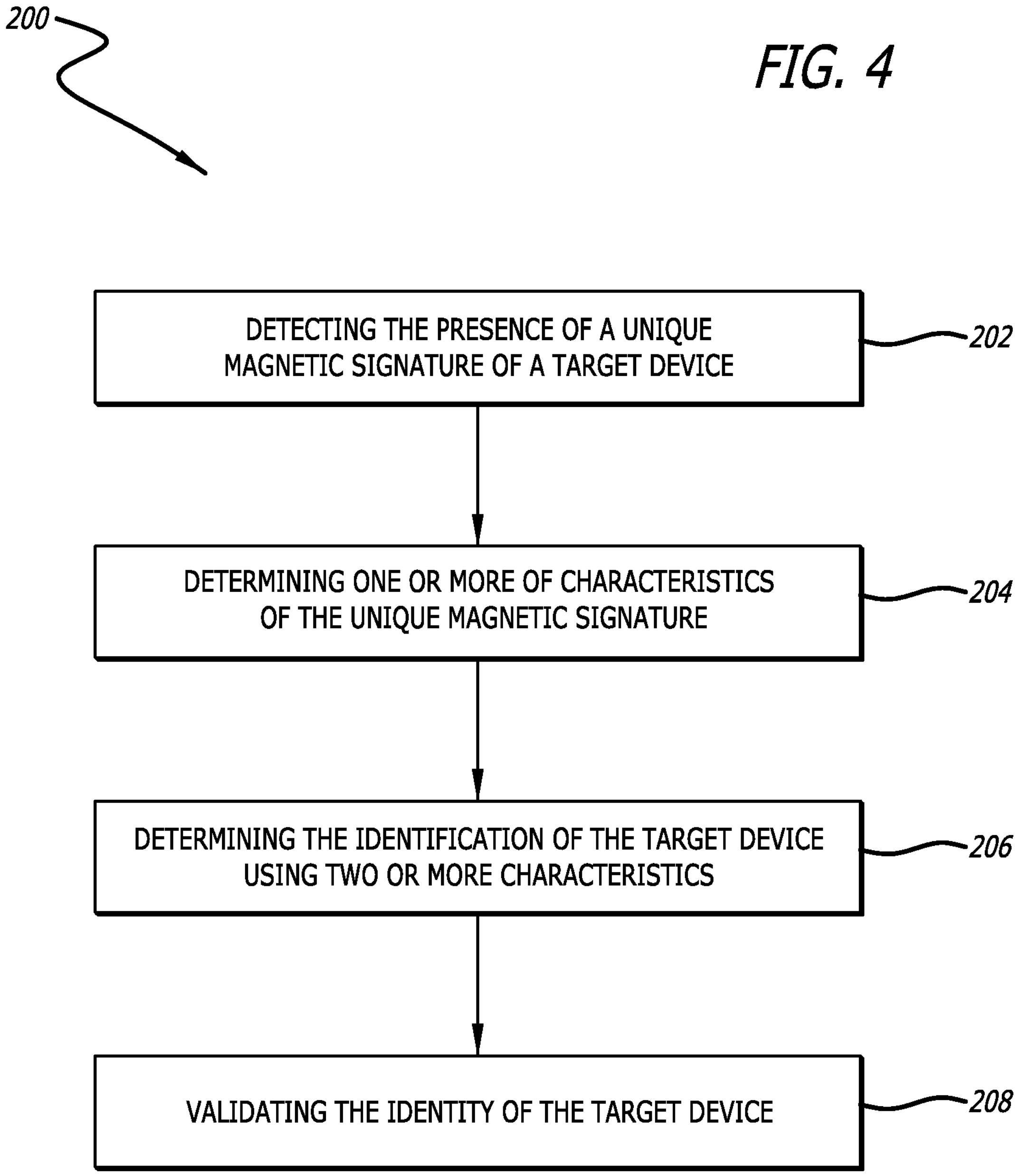
FIG. 4 illustrates a flow chart of an exemplary method of identifying a target medical device based upon the magnetic signature, in accordance with some embodiments.

FIG. 4 illustrates a flow chart of the exemplary method 200 of identifying the target medical device 140 based on the magnetic signature 150 of the target medical device 140, in accordance with some embodiments. In some embodiments, the method 200 includes detecting the presence of a magnetic signature 150 of the target medical device 140 (block 202). In some embodiments, detecting the presence of the magnetic signature 150 includes using the magnetic signature identification system 100 having the magnetic signature identification device 102 to detect the presence of the magnetic signature 150 of the target medical device 140. In some embodiments, the magnetic signature identification device includes one or more magnetometers 110 in communication with the console 120, where the one or more magnetometers 110 are configured to detect the presence of a magnetic signature 150. The magnetic signature 150 may include one or more dipoles imprinted on the target medical device 140 having ferrous elements.

The method 200 further includes determining one or more characteristics of the magnetic signature 150 (block 204). In some embodiments, determining one or more characteristics of the magnetic signature 150 includes determining one or more of: the number of dipoles on the target medical device 140, the orientation of each of the detected dipoles on the target medical device 140, the position of each of the detected dipoles on the target medical device 140, and the length of each of the detected dipoles on the target medical device 140. In some embodiments, the console 120 may be configured to determine the number of dipoles, the orientation of the detected dipoles, the position of the dipoles, and the length of the dipoles, using magnetometer values received from the one or more magnetometers 110. In some embodiments, the console 120 may be configured to generate a detected dipole number value, a dipole length value for each of the detected dipoles, a dipole position value for each of the detected dipoles, and an orientation value for each of the detected dipoles.

The method 200 further includes determining the identification of the target medical device 140 using one or more characteristics (block 206). In some embodiments, determining the identification of the target medical device 140 using one or more characteristics includes correlating one or more of the characteristics with the identification of the target medical device 140. In some embodiments, correlating the one or more characteristics includes correlating two or more characteristics with the identification of the target medical device 140. In some embodiments, correlating one or more of the characteristics with the identification of the target medical device 140 includes the console 120 correlating the one or more characteristics with the identification of the target medical device 140. In some embodiments, the console 120 may be configured to use two or more of: the detected dipole number value, the dipole length value for each of the detected dipoles, the dipole position value for each of the detected dipoles, or the orientation value for each of the detected dipoles to determine the identification of the target medical device 140.

The method 200 further includes validating the identity of the target medical device 140 (block 208). In some embodiments, the console 120 may prompt a user to validate the identity of the target medical device 140 as determined by the magnetic signature 150. In some embodiments, the console 120 may compare the one or more characteristics with a database of target devices 140 with their magnetic signature 150 to validate the identity of the target medical device 140. In some embodiments, the console 120 may compare known values of the magnetic signature 150 includes the number of dipoles, the length of each of the dipoles, the orientation of each of the dipoles, and the position of each of the dipoles to the detected dipole number value, the dipole length value for each of the detected dipoles, the dipole position value for each of the detected dipoles, or the orientation value for each of the detected dipoles to validate the identity of the target medical device 140.

Figure 5:
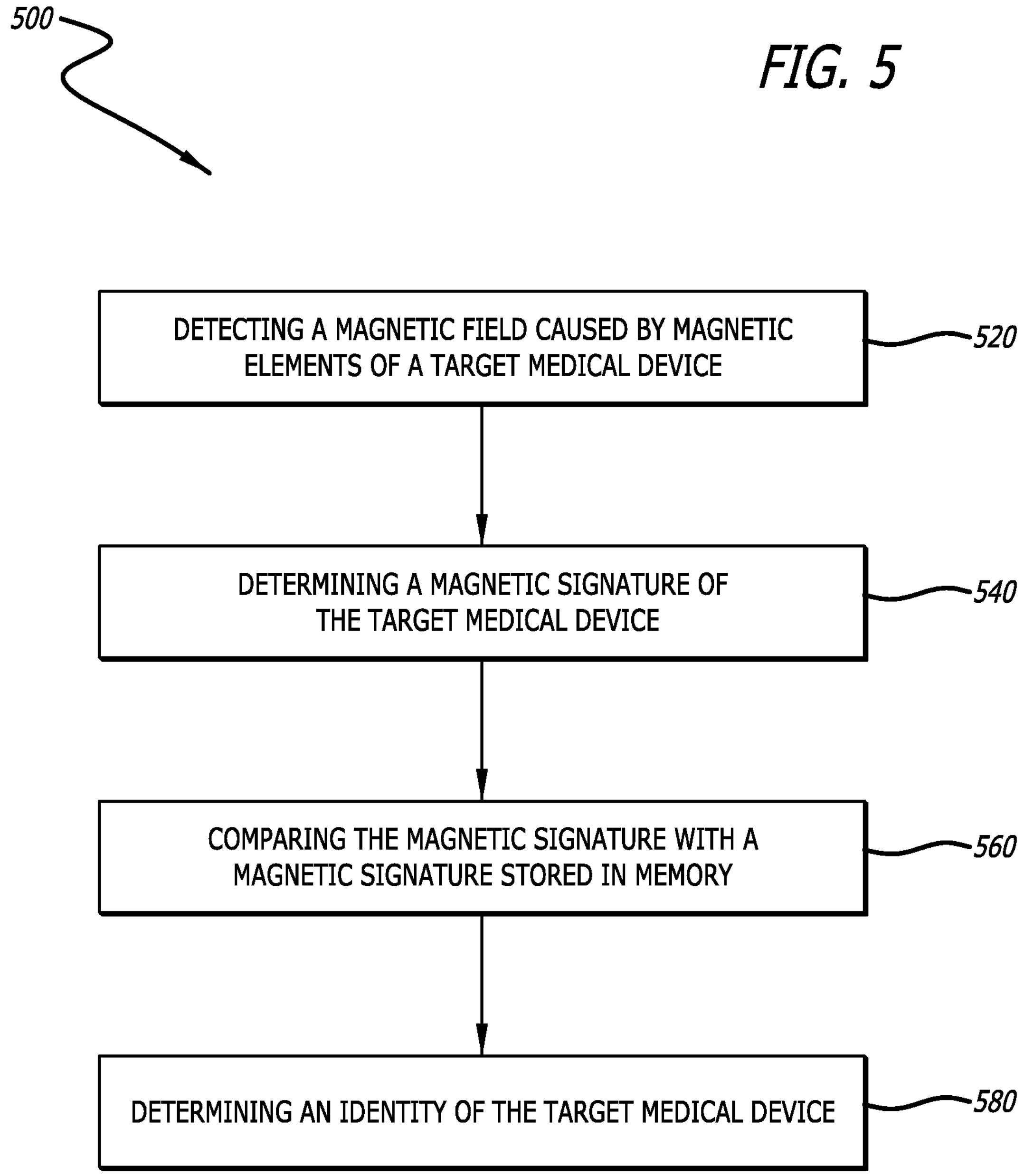
FIG. 5 illustrates a flow chart of another exemplary method for identifying a target medical device, in accordance with some embodiments.

FIG. 5 illustrates a flow chart of another exemplary method as performed by the system 100 for identifying the target medical device. The method 500 may include all or a subset of the following steps or processes.

The method 500 may include detecting a magnetic field caused by the magnetic elements of the target medical device (block 520). More specifically, the magnetometers of the magnetic signature identification device may detect the magnetic field caused by the magnetic elements. The clinician may place the target medical device within a detecting range the magnetometers so that the magnetometers may detect specific characteristics of the magnetic field. In some embodiments, the magnetic field may be combination a multiple magnetic fields defined by multiple magnetic elements.

The method 500 may include determining from the magnetic field a magnetic signature of the target medical device (block 540). More specifically, the logic of the system may derive or determine the magnetic signature of the target medical device as defined by the specific characteristics created/defined by the magnetic elements.

The method 500 may include comparing the magnetic signature with a magnetic signature stored in memory of the system (block 560). In some embodiments, the system may include the identities of multiple medical devices (i.e., optional target medical devices) stored in memory, where each of the multiple medical devices includes a distinct magnetic signature linked thereto. The logic may compare the magnetic signature determined from the target medical device with the magnetic signatures of the multiple medical devices stored in memory.

The method 500 may include determining the identity of the target medical (block 580). As result of the comparison (block 560), the logic may determine the identity of the target medical device when the magnetic signature of the target medical device aligns with (e.g., matches, is the same as, or is similar to) any one of the medical signatures stored in memory. When the magnetic signature of the target medical device aligns with a magnetic signature linked to any the multiple medical devices stored in memory, the logic may determine that the identity of the target medical device is the same as the identity of the medical device whose magnetic signature aligns with the magnetic signature of the target medical device.

In some embodiments of the method 500, the magnetic elements of the target medical device may include a number of dipoles located on the target medical device. In such embodiments, determining the magnetic signature may include determining the number of dipoles. In some embodiments of the method 500, determining the magnetic signature may include determining a position of a first dipole on the target medical device with respect to a position of a second dipole on the target medical device.

In some embodiments of the method of the methos 500, determining the magnetic signature may include (i) determining a length of a third dipole on the target medical device, and (ii) determining a length of a fourth dipole on the target medical device, where the length of the fourth dipole is different from the length of the third dipole.

In some embodiments of the method 500, determining the magnetic signature may include (i) determining an orientation of a fifth dipole on the target medical device; and determining an orientation of a sixth dipole on the target medical device, where the orientation of the sixth dipole is different from the orientation of the fifth dipole.

In some embodiments of the method 500, the system may include a plurality of medical devices, where each one of the plurality of medical devices includes a magnetic signature distinct from the magnetic signatures of the other ones of the plurality of medical devices, and where the target medical device is chosen from the plurality of medical devices.

In some embodiments of the method 500, the system may include a medical device tracking system configured to track the location of the target medical device in three-dimensional space via the magnetic signature, and the method 500 may further include tracking the location of the target medical device in three-dimensional space via the magnetic signature.

In some embodiments of the method 500, the medical device tracking system is configured to track two or more target medical devices simultaneously. In such embodiments, the method 500 may further include (i) tracking the location of a first target medical device via the magnetic signature of the first target medical device and (ii) tracking the location of a second target medical device via the magnetic signature of the second target medical device, where the magnetic signature of the second target medical device is distinct from the magnetic signature of the first target medical device.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A medical system, comprising:

a target medical device having a number of magnetic elements defining a magnetic signature, wherein:

the number of magnetic elements include a number of dipoles, and the magnetic signature includes at least one of a manufacturing history or a serial number of the target medical device; and a magnetic signature identification device, comprising:

one or more magnetometers configured to detect a number of magnetic fields defined by the number of magnetic elements; and a console coupled with the one or more magnetometers, the console including one or more processors, an energy source, and a non-transitory computer-readable medium having logic stored thereon that, when executed by the one or more processors, performs operations, including:

receiving electrical signals from the one or more magnetometers, the electrical signals based on the number of magnetic fields; and determining the magnetic signature from the electrical signals, comprising determining:

the number of dipoles;

a position on the target medical device of one or more of the number of dipoles; and at least one of:

a number of two or more dipoles;

an orientation of two or more dipoles;

a length of at least one dipole; or a position of at least a first dipole with respect to at least a second dipole.

2. The medical system according to claim 1, wherein the number of dipoles define a number of magnetic characteristics detectable by the one or more magnetometers.

3. The medical system according to claim 1, wherein the number of magnetic elements are imprinted on the target medical device.

4. The medical system according to claim 2, wherein the number of magnetic characteristics are selected from the group consisting of: the number of dipoles on the target medical device, a position of one or more of dipoles on the target medical device, a length of one or more of dipoles extending along the target medical device, and an orientation of one or more of the dipoles with respect to one or both of (i) the target medical device, and (ii) any other dipole.

5. The medical system according to claim 1, wherein the magnetic signature identification device is coupled with another medical device or system.

6. The medical system according to claim 5, wherein another medical device or system is selected from a group consisting of an ultrasound probe, an ultrasound system, and a patient sensor.

7. The medical system according to claim 1, wherein determining the magnetic signature includes at least two of:

determining the number of two or more dipoles;

determining the orientation of two or more dipoles a first dipole disposed adjacent to and extending distally away from the hub;

determining the length of at least one dipole; or determining a longitudinal position of at least the first dipole with respect to at least the second dipole along a needle.

8. The medical system according to claim 1, wherein the operations further include:

comparing the magnetic signature with a stored magnetic signature in the non-transitory computer-readable medium, the stored magnetic signature linked to a defined medical device identity; and as a result of the comparing, determining that an identity of the target medical device is equal to the defined medical device identity when the magnetic signature is equal to the stored magnetic signature.

9. The medical system according to claim 8, wherein the operations further include communicating the identity of the target medical device to another medical device or system.

10. The medical system according to claim 1, further including a plurality of medical devices, wherein:

each one of the plurality of medical devices includes a magnetic signature distinct from magnetic signatures of other magnetic signatures of the plurality of medical devices, and the target medical device is chosen from the plurality of medical devices.

11. The medical system according to claim 1, wherein the magnetic signature identification device is coupled with a medical device tracking system configured to track a location of the target medical device in three-dimensional space via the magnetic signature.

12. The medical system according to claim 11, wherein:

the medical device tracking system is configured to track two or more target medical devices simultaneously, and each of the two or more target medical devices has a magnetic signature that is distinct from another target medical devices.

13. The medical system according to claim 1, wherein one of the number of dipoles is disposed at a proximal end of the target medical device.

14. The medical system according to claim 1, wherein the number of dipoles includes:

the first dipole located at a distal tip of the target medical device;

the second dipole located at a proximal end of the target medical device; and a third dipole located at a midpoint between the proximal end and the distal tip.

15. A method performed by a medical system of identifying a target medical device, comprising:

detecting a magnetic field caused by magnetic elements of the target medical device;

determining from the magnetic field a magnetic signature of the target medical device, the magnetic signature including at least one of a manufacturing history or a serial number of the target medical device, wherein:

the magnetic elements of the target medical device include a number of dipoles located on the target medical device, and determining the magnetic signature includes:

determining the number of dipoles; and determining a position on the target medical device of one or more of the number of dipoles;

comparing the magnetic signature determined from the magnetic field with a magnetic signature stored in memory of the medical system, the magnetic signature stored in memory linked to a defined medical device identity; and as a result of the comparing, determining that an identity of the target medical device is equal to the defined medical device identity.

16. The method according to claim 15, wherein determining the magnetic signature includes determining the number of dipoles.

17. The method according to claim 15, wherein determining the magnetic signature includes determining a relative position of a first dipole on the target medical device with respect to a second dipole on the target medical device.

18. The method according to claim 15, wherein determining the magnetic signature includes:

determining a length of a third dipole on the target medical device, determining a length of a fourth dipole on the target medical device, wherein the length of the fourth dipole is different from the length of the third dipole.

19. The method according to claim 15, wherein determining the magnetic signature includes:

determining an orientation of a fifth dipole on the target medical device, and determining an orientation of a sixth dipole on the target medical device, wherein the orientation of the sixth dipole is different from the orientation of the fifth dipole.

20. The method according to claim 15, wherein:

the medical system includes a plurality of medical devices, each one of the plurality of medical devices includes a magnetic signature distinct from the magnetic signatures of other magnetic signatures of the plurality of medical devices, and the target medical device is chosen from the plurality of medical devices.

21. The method according to claim 15, wherein the medical system includes a medical device tracking system configured to track a location of the target medical device in three-dimensional space via the magnetic signature, the method further comprising tracking the location of the target medical device in three-dimensional space via the magnetic signature.

22. The method according to claim 21, wherein:

the medical device tracking system is configured to track two or more target medical devices simultaneously, the method further comprising:

tracking a location of a first target medical device via a magnetic signature of the first target medical device; and tracking a location of a second target medical device via a magnetic signature of the second target medical device, wherein the magnetic signature of the second target medical device is distinct from the magnetic signature of the first target medical device.

23. A medical device, comprising:

a plurality of magnetic elements coupled to a body of the medical device, the plurality of magnetic elements defining a magnetic signature of the medical device, the magnetic signature including at least one of a manufacturing history or a serial number of the medical device, wherein:

the medical device is one of a plurality of medical devices of a medical system;

each medical device includes a magnetic signature that is distinct from magnetic signatures of other medical devices of the medical system, the plurality of magnetic elements include a number of dipoles defining a number of magnetic characteristics of the magnetic signature, and the number of magnetic characteristics include:

the number of dipoles; and a position on the medical device of one or more of the number of dipoles.

24. The medical device according to claim 23, wherein the number of magnetic elements are imprinted on the medical device.

25. The medical device according to claim 23, wherein the number of magnetic characteristics include a relative position on the medical device of one dipole with respect to at least one other dipole.

26. The medical device according to claim 23, wherein the number of magnetic characteristics include a length of one or more of the number of dipoles.

27. The medical device according to claim 23, wherein the number of magnetic characteristics include an orientation of one or more of the number of dipoles.

* * * * *